US006478735B1

(12) United States Patent
Pope et al.

(10) Patent No.: US 6,478,735 B1
(45) Date of Patent: Nov. 12, 2002

(54) PHYSIOLOGICAL FEEDBACK METHOD AND SYSTEM

(75) Inventors: Alan T. Pope, Poquoson, VA (US); Kurt E. Severance, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/494,160

(22) Filed: Jan. 28, 2000

Related U.S. Application Data

(60) Provisional application No. 60/118,772, filed on Jan. 28, 1999, and provisional application No. 60/170,784, filed on Dec. 15, 1999.

(51) Int. Cl.[7] .............................. A61B 5/00; A61B 5/02; G06K 9/00
(52) U.S. Cl. ...................... 600/300; 600/481; 382/128
(58) Field of Search ................................ 600/300, 455, 600/508, 407, 451, 425, 410, 481, 549, 587, 346, 586; 382/8, 12, 130

(56) References Cited

U.S. PATENT DOCUMENTS

| 3,641,993 A | | 2/1972 | Gaarder et al. | |
| 3,916,876 A | | 11/1975 | Freeman | |
| 4,170,225 A | | 10/1979 | Criglar et al. | |
| 4,771,467 A | * | 9/1988 | Catros et al. | 382/197 |
| 5,045,935 A | | 9/1991 | Kikuchi | |
| 5,050,604 A | * | 9/1991 | Reshef et al. | 600/573 |
| 5,140,992 A | | 8/1992 | Zuckerwar et al. | |
| 5,174,299 A | * | 12/1992 | Nelson | 600/549 |
| 5,261,404 A | | 11/1993 | Mick et al. | |
| 5,273,038 A | | 12/1993 | Beavin | |
| 5,282,471 A | * | 2/1994 | Sato | 600/455 |
| 5,343,871 A | | 9/1994 | Bittman et al. | |
| 5,377,100 A | | 12/1994 | Pope et al. | |
| 5,429,140 A | | 7/1995 | Burdea et al. | |
| 5,465,729 A | | 11/1995 | Bittman et al. | |
| 5,482,051 A | | 1/1996 | Reddy et al. | |
| 5,524,631 A | | 6/1996 | Zahorian et al. | |
| 5,546,943 A | | 8/1996 | Gould | |
| 5,577,510 A | | 11/1996 | Chittum et al. | |
| 5,588,428 A | | 12/1996 | Smith et al. | |
| 5,701,897 A | * | 12/1997 | Sano | 600/451 |
| 5,840,023 A | * | 11/1998 | Oraevsky et al. | 600/586 |
| 5,879,312 A | * | 3/1999 | Imoto | 600/587 |
| 6,166,740 A | * | 12/2000 | Malzbender | 382/128 |

FOREIGN PATENT DOCUMENTS

WO     WO 96/13207     * 5/1996

* cited by examiner

Primary Examiner—Eric F. Winakur
Assistant Examiner—David McCrosky
(74) Attorney, Agent, or Firm—Helen M. Galus (57) ABSTRACT

A method and system provide physiological feedback for a patient and/or physician. At least one physiological effect experienced by a body part of a patient is measured non-invasively. A three-dimensional graphics model serving as an analogous representation of the body part is altered in accordance with the measurements. A binocular image signal representative of the three-dimensional graphics model so-altered is displayed for the patient and/or physician in a virtual reality enviromnent.

53 Claims, 5 Drawing Sheets

FIG. 5A Tapered Cylinder Without Cap

FIG. 5B Tapered Cylinder With Hemispherical Cap

FIG. 5C Tapered Cylinder With Adjacent Vessel

PHYSIOLOGICAL FEEDBACK METHOD AND SYSTEM

CLAIM OF BENEFIT OF PROVISIONAL APPLICATION

Pursuant to 35 U.S.C. Section 119, the benefit of priority from provisional application No. 60/118,772, with a filing date of Jan. 28, 1999, and provisional application No. 60/170,784, with a filing date of Dec. 15, 1999, is claimed for this non-provisional application.

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

This invention relates to physiological feedback systems and methodologies. More specifically, the invention is a method and system for providing physiological feedback to a patient and/or physician in real time and in a way that allows the patient to relate his overall emotional and/or physical sensation with a monitored physiological effect.

2. Description of the Related Art

Both biofeedback and physiological feedback systems and methods traditionally transform and display physiological information or effects in graph or chart form. The physiological information (e.g., temperature, blood pressure, etc.) can be obtained from skin surface sensors. The displayed graph or chart typically displays a value (e.g., temperature, blood pressure, etc.) measured by the sensor(s) as a function of time. While this type of data provides the medical professional with diagnostic information, it does not present information in a way that is easily interpreted by the patient. That is, the patient is not presented with an understandable representation of the ultimate physiological effect (e.g., blood flow, muscle contraction, sweat production, intestinal or stomach activity, etc.) being experienced by the patient. Accordingly, the patient is unable to relate internally-occurring physiological effects with his or her general physical and emotional sensation experience occurring at the same time.

U.S. Pat. Nos. 5,273,038 and 5,503,149 disclose the computer simulation of a live organ (e.g., the heart) using a variety of sensed electrical signals indicative of the beginning of activity of the particular organ. The electrical signals are processed/displayed to present an image of the organ performing its function. However, an image of the internal organ activity based on the initiating electrical event does not give the patient the feedback he or she needs to visualize and understand the ultimate physical effects that they are experiencing as a result of the organ activity.

SUMMARY OF THE INVENTION

Accordingly, it is an object of the present invention to provide a method and system that allows a patient to relate their overall general sensations with a specific physiological effect for physiologic education and/or biofeedback purposes.

Another object of the present invention is to provide a real-time physiological feedback system so that a patient can receive feedback regarding a physiological effect as it is being experienced.

Still another object of the present invention is to provide a physiological feedback method and system that presents a patient with a view of an internal physiological effect using non-invasive measurement techniques.

Yet another object of the present invention is to provide a physiological feedback method and system that immerses the patient in a feedback image environment to reduce or eliminate outside distractions.

Still another object of the present invention is to provide a physician a tool that satisfies the above objects for use in distinguishing various types of physiological dysfunction and for observing the progress of a disease process and the effects of a treatment intervention.

Other objects and advantages of the present invention will become more obvious hereinafter in the specification and drawings.

In accordance with the present invention, a method and system provide physiological feedback for a patient. At least one physiological effect experienced by a body part of a patient is measured non-invasively in terms of a time-series of discrete signals representing the physiological effect over a period of time. A three-dimensional graphics model is stored in a stereographic processor capable of generating a binocular image signal. The three-dimensional graphics model is an essentially analogous representation of the body part. Each discrete signal is processed using the stereographic processor to alter the three-dimensional graphics model. The binocular image signal output by the stereographic processor is representative of the three-dimensional graphics model so-altered. The three-dimensional graphics model so-altered is displayed for the patient and/or physician in a virtual reality environment.

DETAILED DESCRIPTION OF THE INVENTION

Figure 1:
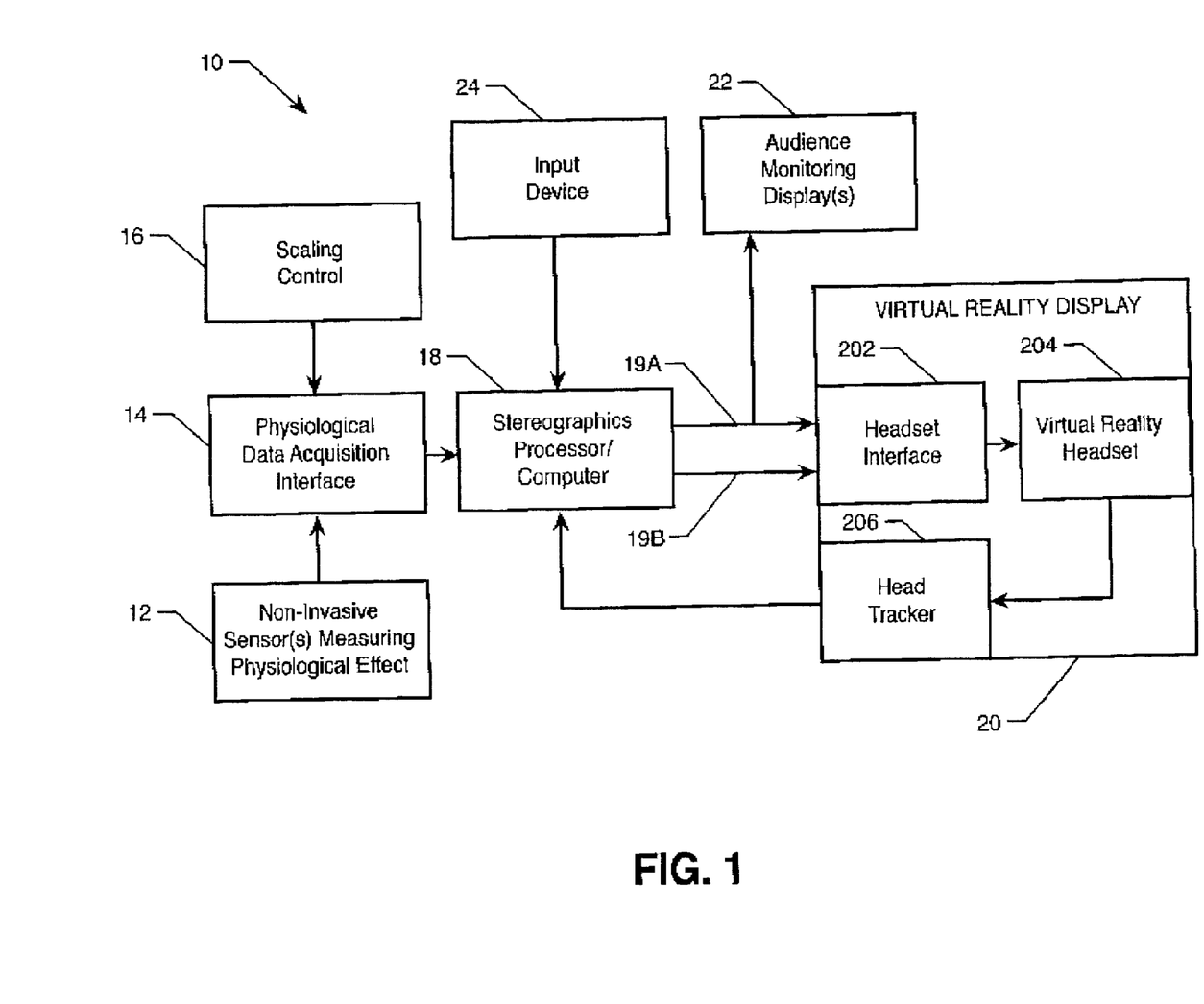
FIG. 1 is a top-level block diagram of an embodiment of the physiological feedback system according to the present invention.

Referring now to the drawings, and more particularly to FIG. 1, a top-level block diagram of an embodiment of the physiological feedback system according to the present invention is shown and referenced generally by numeral 10. System 10 and the method of operation thereof will be explained herein by way of illustrative example as it relates to blood movement or flow. However, as will be explained further below, the present invention can be used to present physiological feedback information for other physiological effects such as muscle deformation, perspiration production, digestive sounds, heart sounds, etc. In each case, the physiologic effect being experienced by the patient is presented to the patient and/or their physician, or other viewer, in real-time. In terms of the patient, he or she can thereby relate their own general physical and/or emotional state to a particular physiological effect. As a result, the present invention can be used to educate a patient about the severity, degradation or improvement of a physical condition. The present invention can also be used as part of biofeedback training. That is, the patient can visualize how their current emotional state affects a particular physiological effect.

System 10 has one or more non-invasive sensors 12 coupled to a patient's skin surface in an area of interest. In terms of measuring the physiological effect of blood flow, sensors 12 could be a thermistor for measuring temperature and a photoplethysmograph (PPG) for measuring blood volume pulse of the patient. The use of temperature and blood volume pulse individually as a means of determining blood flow is well known in the art. In the present invention, temperature can be used to monitor slow changes in blood flow and blood volume pulse can be used to monitor fast changes in blood flow. The combination of these two measurements enables a full characterization of blood flow. Further, other sensors or combinations thereof can be used to determine blood flow without departing from the scope of the present invention. Sensors 12 would typically be placed on the skin in an area of extensive superficial vascularization. e.g., a body extremity such as a fingertip or toe, etc., or placed on the skin at a point where an artery or vein passes close to the surface of the skin.

The physiological effects detected by sensors 12 over a period of time are transduced/converted to analog electrical signals which are passed on to a physiological data acquisition interface 14. At interface 14, the analog signals are digitized into discrete signals. If the discrete signals require manual amplitude adjustment during operation, a scaling control 16 can be coupled to interface 14. Interface 14 and scaling control 16 are configured to permit independent scaling/amplification of each sensed parameter.

The discrete (and, if necessary, amplified) signals from interface 14 are provided to a stereographics processor/computer 18 which typically includes a programmable digital computer, a monitor, a keyboard and a mouse. Some of the features preferably required of computer 18 by the present invention include a serial port interface for receiving discrete signals from interface 14, two video graphics adaptor (VGA) ports for outputting left and right (i.e., binocular) image signals, at least one ISA slot (for the interface board of head tracker 206 described below), a high-speed processor such as Intel's PENTIUM II processor, an operating system such as Microsoft's WINDOWS NT, and a sufficient amount of random access memory (RAM). It is further preferred that computer 18 include a computer graphics accelerator capable of rendering left and right three-dimensional views of an image. One commercially-available graphics accelerator is the REALIZM board from Intergraph Computer Systems, Huntsville, Ala. Each left and right view is preferably constructed at a rate of at least 50,000 polygons/second. Such computers are easily constructed using commercially available hardware. Computer 18 could also be realized with a UNIX workstation capable of generating enhanced three-dimensional graphics. One such workstation is the OCTANE available commercially from Silicon Graphics, Mountain View, Calif.

Operationally, computer 18 stores a three-dimensional graphics model that is an analogous representation of the patient's body part experiencing the physiological effect being monitored. In terms of blood flow, the stored three-dimensional graphics model is an analogous representation of a section of a vascular branch or network such as an artery-to-vein interface, the details of which will be explained further below. Computer 18 outputs left and right image signals 19A and 19B, respectively, of the model to a virtual reality display system 20. Further, computer 18 processes the discrete signals it receives from interface 14 to alter the model in accordance therewith. Computer 18 also processes inputs from a head tracker (explained further below) representing the current head orientation of the viewer immersed in display system 20 in order to alter the viewer's perspective of the model so-displayed. That is, virtual reality display system 20 receives head-tracked left and right image signals of the model undergoing change that is dictated by the physiological effects (e.g., blood flow) being sensed by sensors 12.

Virtual reality display system 20 is any three-dimensional display system that can be viewed or worn by the patient so that the patient is immersed in an interactive three-dimensional display environment. This encourages the patient to concentrate, isolate, visualize and explore his or her current overall physical and/or emotion sensation relative to the physiological effect being experienced/monitored. It is to be further understood that a physician or any viewer other than the patient could be monitoring display system 20 along with the patient or exclusive of the patient. For example, it may be desirable for the physician to be immersed in display system 20 so that he or she can change/explore various image perspectives along with or exclusive of the patient depending on the patient's physical and/or emotional state.

While a variety of such virtual reality display systems can be constructed/used in the present invention, one such system will be explained herein by way of example. Left and right image signals 19A and 19B, respectively, are input to a headset interface 202 before being supplied to a virtual reality headset 204. One such interface 202 and headset 204 combination is the "V8" helmet available from Virtual Research Systems, Santa Clara, Calif. A head tracker 206 is also included in system 20 to accurately compute the position and orientation of headset 204 worn by the patient and supply same to computer 18. An example of a commercially available head tracker 206 is the INSIDETRAK from Polhemus, Colchester, Vt.

System 10 can optionally include one or more monitors 22 coupled to receive one or both of left and right image signals 19A and 19B, respectively. Monitor 22 could provide an audience (e.g., doctors, nurses, students, etc.) a simultaneous display of the imaged physiological effect being experienced by the patient. The display could also be transmitted/viewed remotely via a network such as the internet. Such third-party monitoring could be used for patient evaluation, teaching purposes, etc.

System 10 could also include an input device 24, e.g., keyboard, mouse, joystick, voice control, etc., coupled to computer 18 to provide the equivalent of head tracker signals thereto. That is, input device 24 could be used to control viewing perspective of, for example, display(s) 22. Such control could be independent of head tracker signals received from head tracker 206 to suit the desires of a viewer other than the viewer immersed in display system 20.

As mentioned above, the three-dimensional graphics model altered by computer 18 is an analogous representation of the physiological effect being experienced by the patient. Accordingly, the model and resulting image generated therefrom in display 20 will vary depending on the physiological effect being monitored. For example, in terms of blood flow, the model represents a vascular network. A preferred embodiment of the vascular network at the artery-vein interface used in the present invention will now be explained with additional reference to FIG. 2 where the model is referenced generally by numeral 100. Model 100 will be discussed herein in terms of the image produced thereby. While the software construction of model 100 can be achieved using a variety of commercially available graphics programming environments, one way of constructing model 100 will be described later below.

Figure 2:
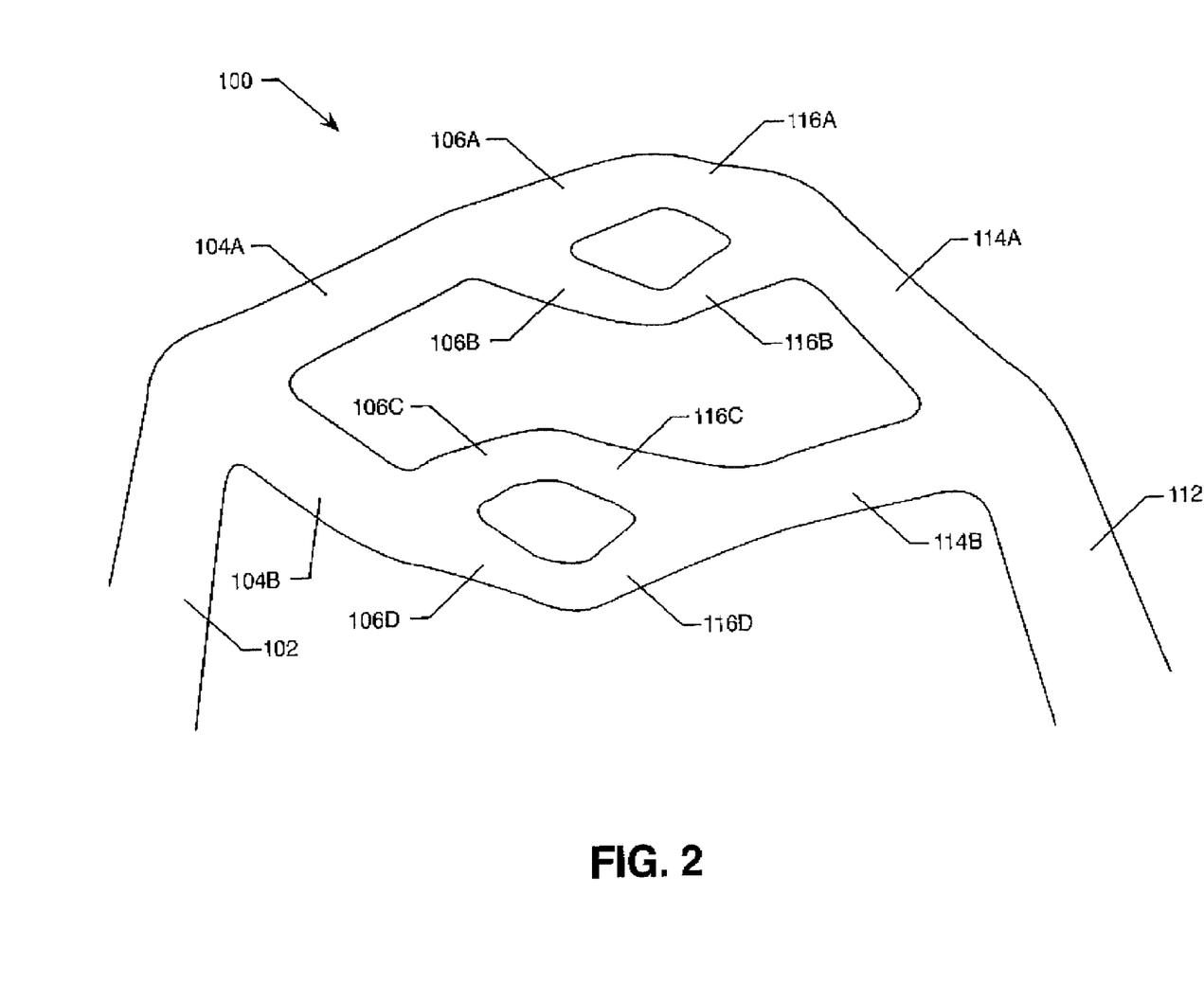
FIG. 2 is a two-dimensional graphic depiction of a model used in the present invention to depict the artery-to-vein interface when the present invention is used to provide blood flow feedback to a patient.

Model 100 is essentially composed of a first three-dimensional structure representative of arteries and a second three-dimensional structure representative of veins. More specifically, the arteries are represented by a first tree-like structure having a trunk 102, primary branches 104A and 104B coupled to trunk 102, and secondary branches 106A–106D with branches 106A and 106B being coupled to branch 104A and branches 106C and 106D being coupled to branch 104B. The veins are represented by a second treelike structure having a trunk 112, primary branches 114A and 114B coupled to trunk 112, and secondary branches 116A–116D with branches 116A and 116B being coupled to branch 114A and branches 116C and 116D being coupled to branch 114B. Finally, secondary (artery) branches 106A–106D terminate at respective ones of secondary (vein) branches 116A–116D.

Figure 3A:
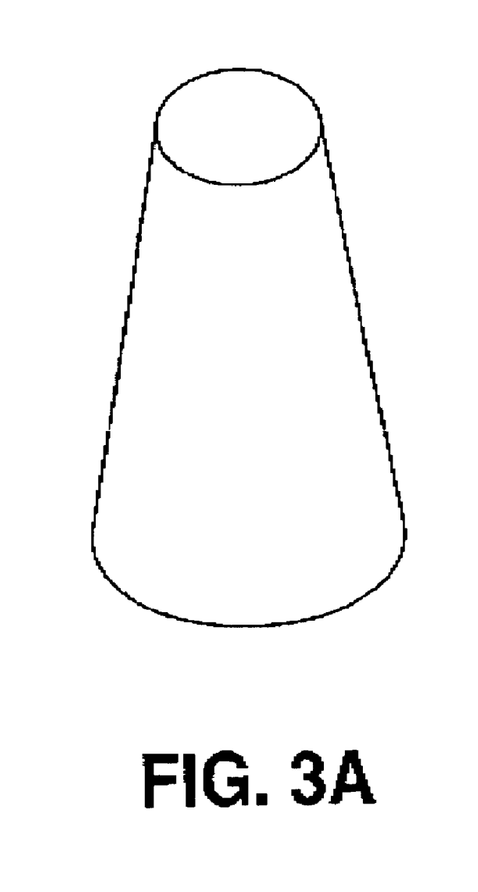
FIG. 3A is a graphic depiction of a perspective view of an embodiment of an "ideal" tapered cylinder which can be used in at least one embodiment of the present invention, for example, as depicted in the model shown in FIG. 2.
Figure 3B:
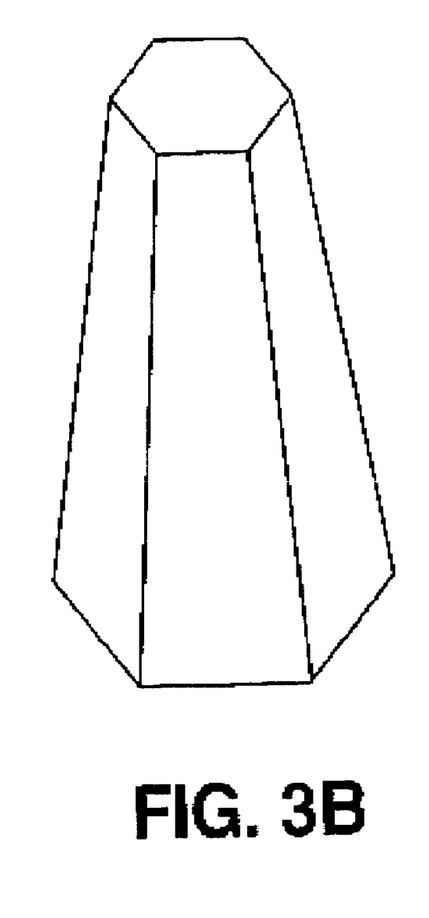
FIG. 3B is a graphic depiction of a perspective view of a simplified polygonalized cylinder which can be used in at least one embodiment of the present invention, for example, as depicted in the model shown in FIG. 2.

It is desirable to simulate the narrowing diameter of arteries as they branch out and ultimately reach their termination point as well as the expanding diameter of veins as a function of their distance from a coupling artery. To do this in a graphically simple manner, each branch of model 100 can be constructed as a cylinder that is linearly tapering (in the case of artery branches) or expanding (in the case of vein branches) in diameter. FIG. 3A shows an embodiment of a preferred ideal smooth shape of a tapered cylinder. FIG. 3B shows a more simplified version of the cylinder with polygonal sides, which, as known in the art, is generally required by a computer graphics processor. As the number of sides to the cylinder increases the smooth shape shown in FIG. 3A is approached.

The properties of each branch can be saved to and retrieved from a file stored in computer 18. By placing the branches end-to-end as illustrated in FIG. 2, a network of simulated arteries and veins is constructed. A curved or splined transition is formed along the outside edges of adjoining branches (see FIG. 5C). While this can be accomplished in a variety of ways using graphics tools, one way of creating such splined transitions is to use some or all of hemispherical "caps" which are standard filler tools/elements available in graphics programming environments. Another way to create such splined transitions is to use non-uniform rational B-splines (NURBS). The three-dimensional aspects of model 100 can be enhanced by applying specular lighting properties to each branch.

To render model 100 in real-time and simulate the expansion and contraction of the blood vessels from blood being pumped through them, the geometric shape, orientation and diametric scale of each branch is encoded in an efficient data structure known as a scene graph. A scene graph is a well-known construct in the field of computer graphics. One example of computer graphics software which makes use of scene graphs is the WorldToolKit from the Sense8 Product Line of Engineering Animation Inc. in Mill Valley, Calif. A scene graph allows three-dimensional geometry to be manipulated and rendered in real-time. It contains all the current geometric elements of a computer-generated scene (in the form of standard three-dimensional vertices, polygons, and, if used, colors) as well as position, orientation, and scaling information in the form of matrices. Matrix transforms are accumulated as the scene graph is processed from left to right. A SEPARATOR NODE is used in the scene graph to isolate matrix transforms to a single subtree.

Figure 4:
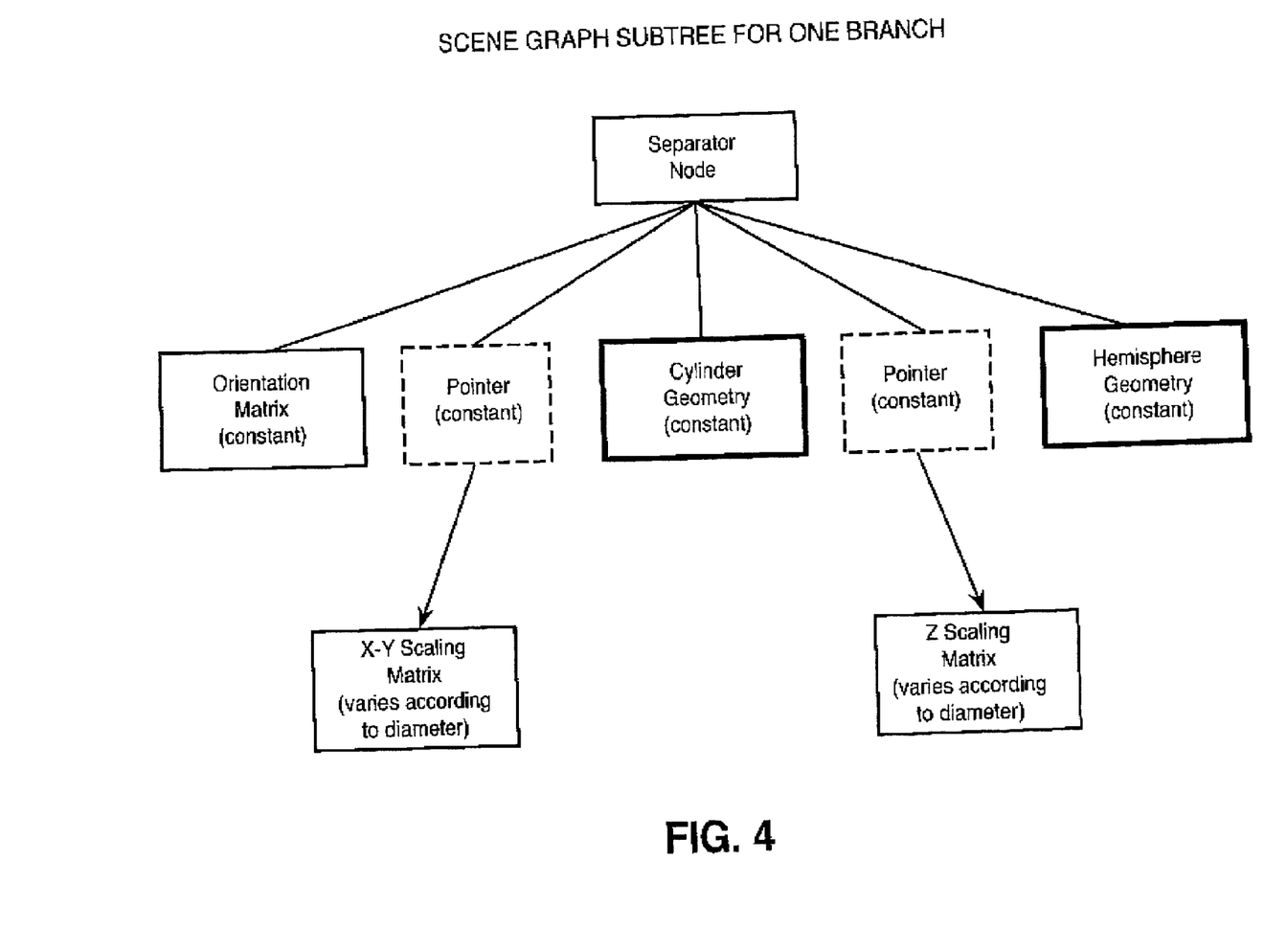
FIG. 4, is a box diagram showing one possible embodiment for a scene graph subtree for one arterial or venous branch.

FIG. 4 is a box diagram showing one possible embodiment for a scene graph subtree for one branch of model 100. Briefly, the baseline shape of each branch of model 100 is a tapered cylinder aligned with the z-axis (as in FIG. 5A) and is encoded in the scene graph of FIG. 4 under CYLINDER GEOMETRY. Similarly, the hemispherical cap (as in FIG. 5B) is encoded in the scene graph under HEMISPHERE GEOMETRY. The translation and rotation of this branch is encoded as a standard four-dimensional transformation matrix under ORIENTATION MATRIX. The current scaling matrix is divided into an X-Y SCALING MATRIX and a Z-SCALING MATRIX as shown. Since the scene graph is processed from left to right, the CYLINDER GEOMETRY will be scaled about only two axes, whereas the HEMISPHERE GEOMETRY will be scaled about all three axes. Every arterial branch is modeled with a similar scene graph subtree. Since all arterial branches are scaled the same, all subtrees can refer to the same X-Y SCALING MATRIX and Z SCALING MATRIX using constant POINTERs. Similar scaling matrices can be implemented for the venous branches.

Pulsating arteries and veins on display 20 can be created by the use of scaling matrices for arteries and veins within the scene graph which change over time. A scaling matrix in the present invention is of the form.

$$\begin{bmatrix} S_x & 0 & 0 & 0 \\ 0 & S_y & 0 & 0 \\ 0 & 0 & S_z & 0 \\ 0 & 0 & 0 & 1 \end{bmatrix}$$

Every branch is initially aligned with the z-axis so that a uniform dilation/expansion of a branch by a scaling factor of D is created by equal scaling in the x and y-dimensions while keeping the z-dimension at unity ($S_x=D$, $S_y=D$, $S_z=1$). Note that the hemispherical "caps" used to create splined transitions between adjoining branches are uniformly scaled in all three dimensions about their centers ($S_x=D$, $S_y=D$, $S_z=D$). The equation for scaling factor D is explained below.

Figure 5A:
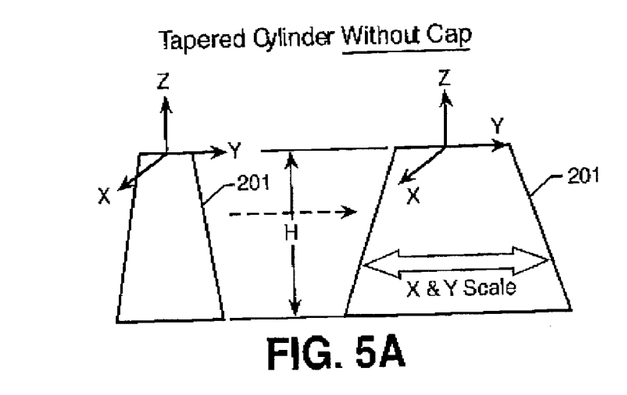
FIG. 5A, a cross-sectional view of a tapered cylinder 201 without a cap, before and after scaling.

As shown in FIG. 5A, a cross-sectional view of a tapered cylinder 201 without a cap, the radius of the cylinder is scaled up or down, but the length, or height "H" remains the same.

Figure 5B:
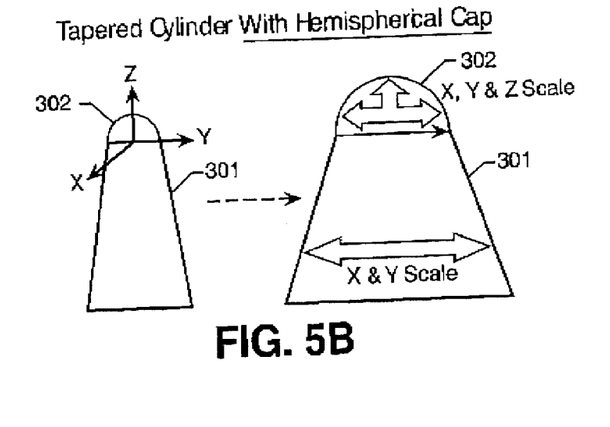
FIG. 5B shows a cross-sectional view of one possible embodiment of a cylinder 301 with a cap 302, before and after scaling.

FIG. 5B shows a cross-sectional view of one possible embodiment of a cylinder 301 with a cap 302, wherein the hemispherical cap is scaled in the x, y, and z axes, and the cylinder is scaled only in the x and y axes.

Figure 5C:
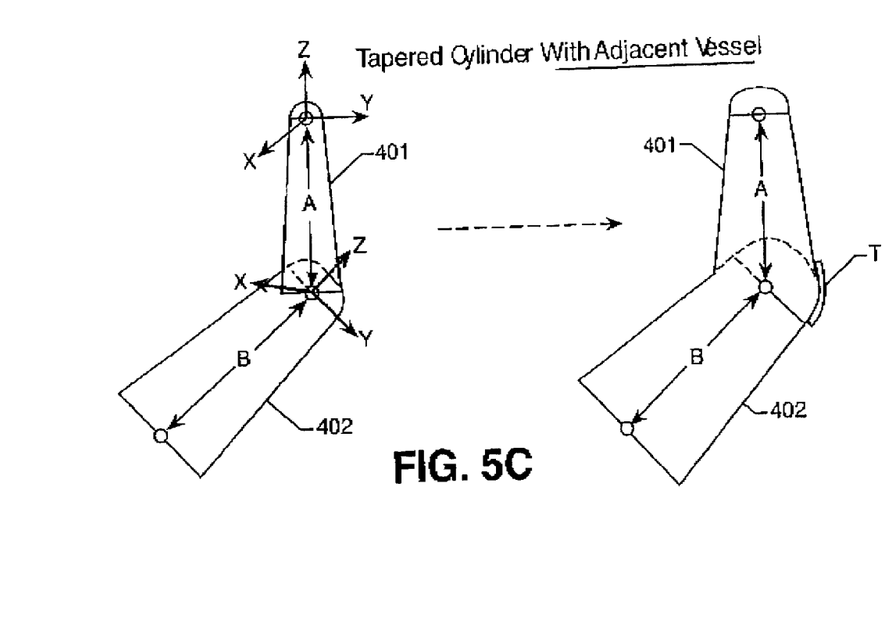
FIG. 5C represents a cross-sectional view of two tapered cylinders 401, 402 representing two adjacent vessels, before and after scaling.

FIG. 5C represents a cross-sectional view of two tapered cylinders 401, 402 representing two adjacent vessels, wherein these cylinders are scaled in their respective x any y axes, while maintaining the respective "A" and "B" heights of the cylinders. A smooth transition T from one branch to the other can be preserved by scaling the hemispherical cap in its respective x, y and z axes.

All arterial branches in the scene can be scaled uniformly along their length (i.e., about their diameter) using the same scaling matrix. As a result, the same diameter scale factor is applied to all artery branches at the same time. Similarly, all venous branches can be scaled uniformly along their length but independently of the arterial branches. To provide the patient with an autokinetic sense of left-to-right movement, the venous side of model 100 is altered using discrete signals (received from interface 14) slightly after the same discrete signals were used to alter the arterial side of model 100. For example, if the display of model 100 is rendered at a resolution of 30 frames per second, the same scaling used on the arterial side in frame 1 is used on the venous side in frame 2. In other words, the venous side would lag the arterial side by one frame in order to create the illusion of flow from the arterial side to the venous side. Note that this visual effect could, for example, be an option turned on or off by the patient.

The pulsating autokinetic sense of movement methodology just described is simple to implement in a real-time fashion without much computational complexity. However, it is to be understood that the present invention is not so limited. For example, a left-to-right moving bulge or pulse in the arterial and venous sides of model 100 could be achieved by scaling at the individual polygonal level as opposed to the branch level just described. Obviously, such scaling comes with a computational cost and a possible loss of real-time feedback. However, it is to be understood that future advances in computer as well as physiological monitoring technologies could be used to improve the spatial and temporal fidelity of this model without departing from the scope of the present invention.

As mentioned above, color can be incorporated into each scene graph. For example, in terms of the illustrative blood flow embodiment, trunk 102 and branches 104A and 104B could be colored red. Branches 106A–106B could be colored red where they couple to branches 104A and 104B and then gradually transition to purple at the point where they couple to a respective one of branches 116A–116D. Branches 116A–116D could gradually transition (from left to right) from purple to blue. Finally, trunk 112 and 114A and 114B could be colored blue. Note that purple is the combination of red and blue and that the shade of purple used during transition will vary with contribution of red and blue. The shading from red-to-purple and then purple-to-blue at the arterial-venous interface branches provides the patient with a smooth visual transition indicative of the actual transition from arteries to veins.

The actual scaling values used to control dynamic changes in branch diameter can be changed as desired. In terms of measuring the patient's temperature and blood volume pulse with sensors 12 and in terms of uniform branch scaling described above, computer 18 can utilize the algorithm in equation below to develop the scaling factor D ($0 < D \leq 1$) for each branch diameter.

$$D = 0.5 \left[ \frac{M_1 - M_{1-\text{MIN}}}{M_{1-\text{MAX}} - M_{1-\text{MIN}}} * \frac{T - T_{\text{MIN}}}{T_{\text{MAX}} - T_{\text{MIN}}} \right] +$$

-continued
$$0.5 \left[ \frac{M_2 - M_{2-\text{MIN}}}{M_{2-\text{MAX}} - M_{2-\text{MIN}}} * \frac{P - P_{\text{MIN}}}{P_{\text{MAX}} - P_{\text{MIN}}} \right]$$

where $M_1$ is the amplification provided by scaling control 16 and applied to the temperature measured by one of sensors 12, $M_{1-MIN}$ is the minimum amplification value of $M_1$, $M_{1-MAX}$ is the maximum amplification value of $M_1$, T is the temperature measured by one of sensors 12, $T_{MIN}$ is the minimum temperature measured, $T_{MAX}$ is the maximum temperature measured, $M_2$ is the amplification provided by scaling control 16 and applied to the blood volume pulse measured by one of sensors 12, $M_{2-MIN}$ is the minimum amplification value of $M_2$, $M_{2-MAX}$ is the maximum amplification value of $M_2$, P is the blood volume pulse measured by one of sensors 12, $P_{MIN}$ is the minimum blood volume pulse measured, and $P_{MAX}$ is the maximum blood volume pulse measured.

Minimum and maximum values are determined by the electrical characteristics of the amplification and measurement equipment. It is to be understood that similar equations could be used for scaling factor D.

The advantages of the present invention are numerous. Physiological effects experienced by a patient are fed back to the patient and/or physician, other viewer, etc., in an immersive display environment in real-time. In this way, the patient can relate their general physical and/or emotional state to a specific physiological effect for educational and/or therapeutic purposes. The sensors used to collect the data are preferably non-invasive thereby minimizing the amount of associated stress on the patient. With the present invention, expensive and time-consuming anatomical imaging methods/systems (e.g., MRI, CAT scan, etc.), as well as the preprocessing of data derived therefrom, are not necessary.

As noted above, the present invention is not limited to blood flow. Another embodiment of the present invention could examine the physiological effect of muscle contraction. In such an embodiment, the length and belly diameter of a graphically-depicted muscle displayed in an immersive display environment could be based on the measurement of the deformation of the skin surface over the muscle with a piezoelectric sensor (i.e., sensor 12), and/or measurement of the stretching of the skin with a strain gauge sensor (i.e., sensor 12). As muscles contract, the skin surface rounds, the muscle shortens and the muscle belly expands thereby stretching the skin over the muscle. Muscle contraction feedback could be useful for the treatment of muscle tension accompanying anxiety and headaches, and for neuromuscular rehabilitation.

Another embodiment involves displaying the action of a graphically depicted sweat gland or sudomotor pump (in an immersive display environment) based on the measurement of the saline saturation of the skin with an electrical conductance sensor (i.e., sensor 12). As sweat glands pump more perspiration onto the skin surface, the conductance of the skin increases. Skin conductance biofeedback could be employed in the treatment of anxiety and hyperhidrosis.

Still another embodiment involves displaying the action of a graphically-depicted stomach, intestine or bowel, or analogous representation thereof, based on acoustic measurements made at the skin surface. Stomach or intestinal activity generates noises that could be easily detected with sensitive microphones (i.e., sensors 12) properly placed on the patient's skin.

Yet another embodiment of the present invention involves displaying the action of graphically-depicted heart valves and/or heart structures, or analogous representations thereof, based on acoustic measurements made at the surface of the patient's torso. The heart action could be modeled to mimic a physician's mental visualization associated with turbulence in heart sounds normally heard with a stethoscope. Heart dynamic anomalies could thus be visually rendered. A related embodiment would involve displaying restricted blood flow due to vessel narrowing. Blood flow in a monitored blood vessel, or analogous representation thereof, could be graphically-depicted based on acoustic measurements made at the surface of the skin over the vessel. The blood flow dynamical display could be modeled to mimic a physician's mental visualization associated with turbulence in blood flow normally heard with a stethoscope. Other mental visualizations employed by the physician from signs sensed at the patient's skin surface during the physical examination could be supplemented by electronic display using the method of the present invention.

Temperature and blood volume pulse biofeedback can, for example, be used for general relaxation training, as well as treatment for a number of vascular problems, such as Raynaud's disease, migraine headache, vasoconstriction secondary to diabetes and connective tissue disease, and hypertension.

A pseudo-code for one possible embodiment of the software is as follows:

```
PHYSIO_DEVICE_INITIALIZE;
PHYSIO_DEVICE_REQUEST_PACKET;
HEAD_TRACKER_INITIALIZE;
HEAD_TRACKER_REQUEST_PACKET;
SCENE_GRAPH_INITLALIZE;
DO {
    PHYSIO_DEVICE_READ_PACKET (TEMP, BVP,
        DIAL1, DIAL2);
    HEAD_TRACKER_READ_PACKET (HEAD_POS,
        HEAD_ORIENT);
    DIAMETER=0.5 * (DIAL1_DIAL1_MIN) / (DIAL1_
        MAX_DIAL1_MIN) * (TEMP_TEMP_MIN) /
        (TEMP_MAX_TEMP_MIN) +0.5 * (DIAL2_
        DIAL2_MIN) / (DIAL2_MAX_DIAL2_MIN) *
        (BVP_BVP_MIN) / (BVP_MAX_BVP_MIN);
    SCENE_GRAPH_MODULATE_SCALE_
        MATRICES (DIAMETER);
    PHYSIO_DEVICE_REQUEST_PACKET;
    HEAD_TRACKER_REQUEST_PACKET;
    UPDATE_PICTURE (SCENE_GRAPH, HEAD_POS,
        HEAD_ORIENT)
}
UNTIL (FINISHED)
```

Thus, although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A physiological feedback system comprising:
    means for measuring at least one physiological effect experienced by a body part of a patient in terms of a time-series of discrete signals representing said physiological effect over a period of time;
    a stereographic processor coupled to said means for measuring, said stereographic processor being capable of generating a binocular image signal;
    a three-dimensional graphics model stored in said stereographic processor, said three-dimensional graphics model being an analogous representation of said body part;
    said stereographic processor processing each of said discrete signals and altering said three-dimensional graphics model in accordance therewith, wherein said binocular image signal output by said stereographic processor is representative of said three-dimensional graphics model so-altered; and
    a display coupled to said stereographic processor for displaying said three-dimensional graphics model so-altered.

2. A system as in claim 1 wherein said means for measuring includes at least one non-invasive sensor coupled to the patient.

3. A system as in claim 1 wherein said physiological effect is blood flow, and wherein said means for measuring includes a sensor for measuring temperature of the patient's blood in an area of interest on the patient and a sensor for measuring blood volume pulse of the patient at said area of interest.

4. A system as in claim 1 wherein said physiological effect is muscle deformation, and wherein said means for measuring includes a sensor for measuring deformation of the patient's skin in an area of interest on the patient.

5. A system as in claim 1 wherein said physiological effect is perspiration, and wherein said means for measuring includes a sensor for measuring saline saturation at the skin of the patient in an area of interest on the patient.

6. A system as in claim 1 wherein said physiological effect is intestinal activity, and wherein said means for measuring includes a sensor for measuring, at the skin surface of the patient, acoustic levels produced by the intestinal activity.

7. A system as in claim 1 wherein said physiological effect is mechanical activity of the patient's heart, and wherein said means for measuring includes a sensor for measuring, at the skin surface of the patient, acoustic levels produced by the patient's heart valves and heart structures.

8. A system as in claim 1 wherein said physiological effect is blood flow, and wherein said means for measuring includes a sensor for measuring, at the skin surface of the patient, acoustic levels produced by the patient's blood flow turbulence.

9. A system as in claim 1 wherein said physiological effect is blood flow, and wherein said three-dimensional graphics model comprises:
    graphic means for generating a first image on said display of a first branching-out structure defined by a first trunk that branches out to a first plurality of branches, and for generating a second image on said display of a second branching-out structure defined by a second trunk that branches out to a second plurality of branches; and
    each of said first plurality of branches terminating at a corresponding one of said second plurality of branches, wherein said first trunk and said first plurality of branches are an analogous representation of arteries, and wherein said second plurality of branches and said second trunk are an analogous representation of veins.

10. A system as in claim 9 wherein said first trunk and each of said first plurality of branches are represented by a cylinder tapering linearly in diameter along its length from left to right on said display, and wherein each of said second plurality of branches and said second trunk are represented by a cylinder expanding linearly in diameter along its length from left to right on said display.

11. A system as in claim 10 wherein a splined transition is formed at adjoining ones of said cylinders in each of said first image and said second image.

12. A system as in claim 9 wherein, when viewed from left to right on said display, said first image transitions from a first color to a second color and said second image transitions from said second color to a third color.

13. A system as in claim 12 wherein transition to said second color occurs in said first plurality of branches and transition to said third color occurs in said second plurality of branches.

14. A system as in claim 12 wherein said first color is red, said second color is purple and said third color is blue.

15. A system as in claim 9 wherein said stereographic processor uses said discrete signals to alter said first image independently of said second image, and wherein said first image so-altered by said discrete signals at a given instant from said period of time is displayed before said second image so-altered by said discrete signals at said given instant, whereby a viewer of said display perceives an autokinetic sense of movement from said first image to said second image.

16. A system as in claim 1 wherein said display comprises a virtual reality display.

17. A system as in claim 16 further comprising a monitoring display coupled to said stereographic processor wherein an audience can view said three-dimensional graphics model so-altered.

18. A method of providing physiological feedback comprising the steps of:
 measuring at least one physiological effect experienced by a body part of a patient in terms of a time-series of discrete signals representing said physiological effect over a period of time;
 providing a three-dimensional graphics model stored in a stereographic processor capable of generating a binocular image signal, said three-dimensional graphics model being an analogous representation of said body part;
 processing each of said discrete signals using said stereographic processor to alter said three-dimensional graphics model in accordance with said discrete signals, wherein said binocular image signal output by said stereographic processor is representative of said three-dimensional graphics model so-altered; and
 displaying said three-dimensional graphics model so-altered in a virtual reality environment.

19. A method according to claim 18 wherein said step of measuring is accomplished non-invasively.

20. A method according to claim 18 wherein said physiological effect is blood flow, and wherein said step of providing said three-dimensional graphics model comprises the steps of:
 generating a first image on said virtual reality environment of a first branching-out structure defined by a first trunk that branches out to a first plurality of branches;
 generating a second image on said virtual reality environment of a second branching-out structure defined by a second trunk that branches out to a second plurality of branches; and
 terminating each of said first plurality of branches at a corresponding one of said second plurality of branches, wherein said first trunk and said first plurality of branches are an analogous representation of arteries, and wherein said second plurality of branches and said second trunk are an analogous representation of veins.

21. A method according to claim 20 further comprising the steps of:
 transitioning said first image from a first color to a second color when viewing said first image from left to right; and
 transitioning said second image from said second color to a third color when viewing said second image from left to right.

22. A method according to claim 21 wherein said step of transitioning to said second color occurs in said first plurality of branches, and wherein said step of transitioning to said third color occurs in said second plurality of branches.

23. A method according to claim 21 wherein said first color is red, said second color is purple and said third color is blue.

24. A method according to claim 20 wherein said step of providing said three dimensional graphics model comprises the steps of:
 representing said first trunk and each of said first plurality of branches by a cylinder tapering linearly in diameter along its length from left to right on said display; and
 representing each of said second plurality of branches and said second trunk by a cylinder expanding linearly in diameter along its length from left to right on said display.

25. A method according to claim 24 further comprising the step of creating a splined transition at adjoining ones of said cylinders in each of said first image and said second image.

26. A method according to claim 20 wherein said step of processing comprises the step of using said discrete signals to alter said first image independently of said second image, and wherein said first image so-altered by said discrete signals at a given instant from said period of time is displayed before said second image so-altered by said discrete signals at said given instant, whereby a viewer of said first image and said second image perceives an autokinetic sense of movement from said first image to said second image.

27. A method according to claim 18 wherein said physiological effect is blood flow, and wherein said step of measuring includes the steps of:
 measuring temperature of the patient's blood in an area of interest on the patient; and
 measuring blood volume pulse of the patient at said area of interest.

28. A method according to claim 18 wherein said physiological effect is muscle deformation, and wherein said step of measuring includes the step of measuring deformation of the patient's skin in an area of interest on the patient.

29. A method according to claim 18 wherein said physiological effect is perspiration, and wherein said step of measuring includes the step of measuring saline saturation at the skin of the patient in an area of interest on the patient.

30. A method according to claim 18 wherein said physiological effect is intestinal activity, and wherein said step of measuring includes the step of measuring, at the skin surface of the patient, acoustic levels produced by the intestinal activity.

31. A method according to claim 18 wherein said physiological effect is mechanical activity of the patient's heart, and wherein said step of measuring includes the step of measuring, at the skin surface of the patient, acoustic levels produced by the patient's heart valves and heart structures.

32. A method according to claim 18 wherein said physiological effect is blood flow, and wherein said step of measuring includes the step of measuring, at the skin surface of the patient, acoustic levels produced by the patient's blood flow turbulence.

33. A physiological feedback system comprising:
   means for non-invasively measuring at least one physiological effect experienced by a body part of a patient in terms of a time-series of discrete signals representing said physiological effect over a period of time;
   a stereographic processor coupled to said means for measuring, said stereographic processor being capable of generating a binocular image signal;
   a three-dimensional graphics model stored in said stereographic processor, said three-dimensional graphics model being an analogous representation of said body part;
   said stereographic processor processing each of said discrete signals and altering said three-dimensional graphics model in accordance therewith, wherein said binocular image signal output by said stereographic processor is representative of said three-dimensional graphics model so-altered; and
   a virtual reality display coupled to said stereographic processor and worn by a viewer for immersing the viewer in a display environment of said three-dimensional graphics model so-altered.

34. A system as in claim 33 wherein said physiological effect is blood flow, and wherein said means for measuring includes a sensor for measuring temperature of the patient's blood in an area of interest on the patient and a sensor for measuring blood volume pulse of the patient at said area of interest.

35. A system as in claim 33 wherein said physiological effect is muscle deformation, and wherein said means for measuring includes a sensor for measuring deformation of the patient's skin in an area of interest on the patient.

36. A system as in claim 33 wherein said physiological effect is perspiration, and wherein said means for measuring includes a sensor for measuring saline saturation at the skin of the patient in an area of interest on the patient.

37. A system as in claim 33 wherein said physiological effect is intestinal activity, and wherein said means for measuring includes a sensor for measuring, at the skin surface of the patient, acoustic levels produced by the intestinal activity.

38. A system as in claim 33 wherein said physiological effect is mechanical activity of the patient's heart, and wherein said means for measuring includes a sensor for measuring, at the skin surface of the patient, acoustic levels produced by the patient's heart valves and heart structures.

39. A system as in claim 33 wherein said physiological effect is blood flow, and wherein said means for measuring includes a sensor for measuring, at the skin surface of the patient, acoustic levels produced by the patient's blood flow turbulence.

40. A system as in claim 33 wherein said physiological effect is blood flow, and wherein said three-dimensional graphics model comprises:
   graphic means for generating a first image on said display of a first branching-out structure defined by a first trunk that branches out to a first plurality of branches, and for generating a second image on said display of a second branching-out structure defined by a second trunk that branches out to a second plurality of branches; and
   each of said first plurality of branches terminating at a corresponding one of said second plurality of branches, wherein said first trunk and said first plurality of branches are an analogous representation of arteries, and wherein said second plurality of branches and said second trunk are an analogous representation of veins.

41. A system as in claim 40 wherein said first trunk and each of said first plurality of branches are represented by a cylinder tapering linearly in diameter along its length from left to right on said display, and wherein each of said second plurality of branches and said second trunk are represented by a cylinder expanding linearly in diameter along its length from left to right on said display.

42. A system as in claim 41 wherein a splined transition is formed at adjoining ones of said cylinders in each of said first image and said second image.

43. A system as in claim 40 wherein, when viewed from left to right on said display, said first image transitions from a first color to a second color and said second image transitions from said second color to a third color.

44. A system as in claim 43 wherein transition to said second color occurs in said first plurality of branches and transition to said third color occurs in said second plurality of branches.

45. A system as in claim 43 wherein said first color is red, said second color is purple and said third color is blue.

46. A system as in claim 40 wherein said stereographic processor uses said discrete signals to alter said first image independently of said second image, and wherein said first image so-altered by said discrete signals at a given instant from said period of time is displayed before said second image so-altered by said discrete signals at said given instant, whereby a viewer of said virtual reality display perceives an autokinetic sense of movement from said first image to said second image.

47. A system as in claim 33 further comprising a monitoring display coupled to said stereographic processor wherein an audience can view said three-dimensional graphics model so-altered.

48. A system as in claim 47 further comprising means, coupled to said stereographics processor, for changing viewing perspective of said three-dimensional graphics model so-altered on said monitoring display.

49. A physiological feedback system for the encouragement of self-regulation of at least one physiological effect by a patient, the feedback system comprising:
   means for measuring at least one physiological effect experienced by a body part of a patient in terms of a time-series of signals representing said physiological effect over a period of time;
   a processor coupled to said means for measuring, said processor being capable of generating an image signal;
   a graphics model stored in said processor, said graphics model being a representation of said body part;
   said processor processing each of said signals and altering said graphics model in accordance therewith, wherein said image signal output by said processor is representative of said graphics model as it is being so-altered; and
   a display coupled to said processor for displaying said graphics model as it is being so-altered, to thus encourage self-regulation of the at least one physiological effect by the patient.

50. The feedback system according to claim 49, wherein said signals representing said at least one physiological effect comprise signals resulting from the physical behavior of the body part.

51. A method of providing physiological feedback comprising the steps of:

measuring at least one physiological effect experienced by a body part of a patient in terms of a time-series of discrete signals representing said physiological effect over a period of time;

providing a graphics model stored in a processor capable of generating an image signal, said graphics model being a generic representation of said body part;

processing each of said discrete signals using said processor to alter said graphics model in accordance with said discrete signals, wherein said image signal output by said processor is representative of said graphics model as it is being so-altered; and displaying said graphics model as it is being so-altered in a virtual reality environment.

52. The method according to claim 51 wherein said step of measuring at least one physiological effect experienced by a body part of a patient in terms of a time-series of discrete signals representing said physiological effect over a period of time comprises measuring signals resulting from the physical behavior of the body part.

53. A physiological feedback system comprising:

means for measuring at least one physiological effect experienced by a body part of a patient in terms of a time-series of signals representing said physiological effect over a period of time;

a processor coupled to said means for measuring, said processor being capable of generating an image signal;

a graphics model stored in said processor, said graphics model being a generic representation of said body part;

said processor processing each of said signals and altering said graphics model in accordance therewith, wherein said image signal output by said processor is representative of said graphics model as it is being so-altered; and a display coupled to said processor for displaying said graphics model as it is being so-altered.

\* \* \* \* \*